US005082930A

United States Patent [19]
Nicolotti et al.

[11] Patent Number: 5,082,930
[45] Date of Patent: * Jan. 21, 1992

[54] COUPLING AGENTS FOR JOINING RADIONUCLIDE METAL IONS WITH BIOLOGICALLY USEFUL PROTEINS

[75] Inventors: Robert A. Nicolotti, Somers, N.Y.; Richard T. Dean, Downingtown, Pa.

[73] Assignee: Mallinckrodt Medical, Inc., St. Louis, Mo.

[*] Notice: The portion of the term of this patent subsequent to Mar. 22, 2005 has been disclaimed.

[21] Appl. No.: 275,415

[22] Filed: Nov. 23, 1988

Related U.S. Application Data

[63] Continuation-in-part of Ser. No. 868,800, May 29, 1986, Pat. No. 4,861,869.

[51] Int. Cl.$^5$ ............................................. C07K 3/00
[52] U.S. Cl. ................................... 530/402; 548/341; 548/542; 562/575; 424/1.1; 424/85.91
[58] Field of Search ................... 424/1.1; 435/7, 68, 435/272, 7.1, 960, 968; 436/512, 543, 547; 514/6; 530/387–388, 402, 404–406, 329–331, 345; 534/100, 573, 692; 548/341, 542

[56] References Cited

U.S. PATENT DOCUMENTS

| | | |
|---|---|---|
| 4,027,005 | 5/1977 | Adler et al. . |
| 4,256,726 | 3/1981 | Kato et al. . |
| 4,272,506 | 6/1981 | Schwarzberg . |
| 4,308,249 | 12/1981 | Frank et al. . |
| 4,444,690 | 4/1984 | Fritzberg . |
| 4,659,839 | 4/1987 | Nicolotti et al. . |
| 4,673,562 | 6/1987 | Davison et al. . |
| 4,732,974 | 3/1988 | Nicolotti et al. ................... 530/390 |
| 4,746,505 | 5/1988 | Jones et al. . |
| 4,837,003 | 6/1989 | Nicolotti ............................. 424/1.1 |
| 4,861,869 | 8/1989 | Nicolotti et al. ................... 530/402 |

FOREIGN PATENT DOCUMENTS 2109407 6/1983 United Kingdom .

OTHER PUBLICATIONS

Goldenberg et al., "Use of Radiolabeled Antibodies to Carcinoembryonic Antigen for the Detection and Localization of Diverse Cancers by External Photoscanning", pp. 1384–1388, Jun. 22, 1978, The New England Journal of Medicine.

Gold et al., "Demonstration of Tumor-Specific Antigens in Human Colonic Carcinomata by Immunological Tolerance and Absorption Techniques", pp. 439–461, (Received for Publication, Nov. 16, 1964).

Belitsky et al., "Radionuclide Imaging of Primary Renal-Cell Carcinoma by 1—131-Labeled Antitumor Antibody", pp. 427–430, vol. 19, No. 4, The Journal of Nuclear Medicine, (1978).

"The Retracted Ephapse", vol. II, No. 8087, p. 462, The Lancet, Aug. 26, 1978.

Primary Examiner—Esther L. Kepplinger
Assistant Examiner—Carol A. Spiegel
Attorney, Agent, or Firm—Rothwell, Figg, Ernst & Kurz

[57] ABSTRACT

This invention relates to bifunctional coupling agents useful in forming conjugates with biologically useful molecules, such as antibodies. These conjugates can be complexed with radionuclide metal ions to provide materials useful for in vivo diagnostic and therapeutic applications.

29 Claims, 2 Drawing Sheets

COUPLING AGENTS FOR JOINING RADIONUCLIDE METAL IONS WITH BIOLOGICALLY USEFUL PROTEINS

CROSS REFERENCE TO RELATED APPLICATION

The present application is a continuation-in-part of copending application Ser. No. 868,800, filed May 29, 1986, now U.S. Pat. No. 4,861,869.

BACKGROUND OF THE INVENTION

This invention relates to coupling agents for use in the production of biologically useful molecules labeled with metal ions, particularly radioisotopes of technetium and rhenium. Radiolabeled antibody fragments incorporating the coupling agents of the invention are useful in therapeutic and in vivo diagnostic applications.

The use of radionuclide metal ions in therapeutic and in vivo diagnostic applications has been practiced for some time For example, gamma-emitting radionuclide meta ions, including technetium-99m, have been used in diagiostic scintigraphy for tumor detection. Beta-emitting isotopes, including rhenium-186, rhenium-188 and rhenium-189, can be used therapeutically in the treatment of tumors.

The efficacy of radionuclides in in vivo diagnostic and therapeutic applications depends on the ability to deliver the radionuclide to the site of the target cells. One method of delivering the radionuclide to the site of the target cells entails coupling the radionuclide metal ions to biologically useful molecules, such as antibodies, which selectively recognize and bind unique ligands associated with the target cells. For example, antigens which are known to be produced by or associated with malignant tumor cells can be bound by the antibody-conjugated radionuclide for the purpose of diagnostic imaging or for the purpose of irradiating the tumor to destroy it.

Goldenberg et al. (*N. Engl. J. Med.*, 298:1384–1388 [1978]) describe experiments in which antibodies to carcinoembryonic antigen (CEA), which is a known tumor-associated antigen (Gold et al., *J. Exp. Med.*, 121:439–462 [1965]), were labeled with iodine-131 and injected into patients with a history of cancer. After 48 hours, the patients were scanned with a gamma scintillation camera and tumors were localized by the gamma emission pattern. Similarly, United Kingdom Patent Application GB 2,109,407 describes the use of monoclonal antibodies to tumor-associated antigens, labeled with metallic radionuclides, for in vivo tumor detection and localization.

It has been suggested that radiolabeled antibody fragments, rather than radiolabeled whole antibodies, be used for in vivo diagnostic and therapeutic applications since the fragments may be better able to penetrate to the desired target site and the antibody fragments may minimize problems of immunogenicity and cross-reactivity associated with whole antibodies (see, e.g., U.S. Pat. No. 4,036,945; *Lancet*, Vol. II, No. 8087, 462 [1978]; Belitsky et al., *J. Nucl. Med.*, 19:429 [1978]). Antibody fragments can be produced in several ways. The antibody molecule can be enzymatically treated to remove carboxylterminal portions of the heavy chains (the Fc fragment), leaving a bivalent F(ab')$_2$ fragment, i.e., two Fab' segments joined by one or more disulfide bonds which link the heavy chains. The F(ab')$_2$ fragment can then be selectively reduced at the disulfide bond(s) joining the two heavy chains, resulting in the production of two monovalent Fab' fragments each having a single antigen-binding site.

Antibody molecules contain a number of reactive side chains which can be employed as sites of attachment for binding a radionuclide metal ion to the antibody. For example, the radionuclide can be conjugated to the antibody through a linker molecule which is reactive with the carboxyl groups of aspartic acid or glutamic acid residues, the amino groups of lysine residues, the aromatic groups of tyrosine or histidine residues, or the sulfhydryl groups of cysteines.

While it has been possible to prepare antibodyradionuclide complexes using the procedures of the prior art, none of the complexes produced by these procedures possesses ideal biodistribution properties for use in imaging procedures. In particular, rapid clearance or low uptake of the radionuclide in the liver and kidneys, which is a desirable property of a good radiographic agent, has been a serious problem with a number of antibody-radionuclide complexes produced by the prior art procedures.

SUMMARY OF THE INVENTION

This invention provides bifunctional coupling agents useful in forming conjugates with biologically useful protein or polypeptide molecules, such as antibodies, which can be complexed with radionuclide metal ions, particularly with isotopes of technetium or rhenium, to provide materials useful for in vivo diagnostic and therapeutic applications. The antibody conjugate of the invention, which is produced by reacting a bifunctional coupling agent of the invention with the $\epsilon$-amino group of a lysine residue in an antibody or an antibody fragment, retains the antigen-binding activity, i.e., immunoreactivity, of the antibody from which it is derived. The bifunctional coupling agent contains an activating group which reacts with an $\epsilon$-amino group of an antibody or an antibody fragment via an acylation reaction to form an amide bond. The bifunctional coupling agent also has a group which is capable of forming a chelate complex with the radionuclide metal ion.

The antibody conjugates which incorporate the coupling agents of the invention can be represented by the general formulas:

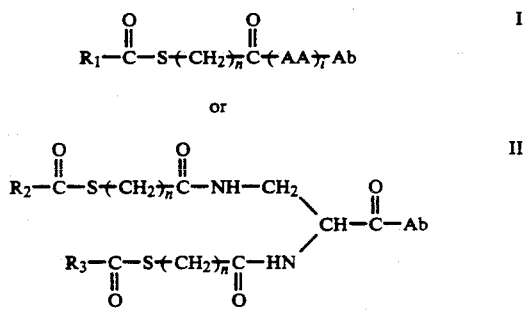

wherein Ab is the residue of an antibody or fragment thereof; $R_1$, $R_2$, and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently- $\alpha$ or $\beta$ amino acids linked to each other by amide bonds; and i is an integer of from 2 to 6.

The antibody conjugate of formulas I or II is complexed with a radionuclide, e.g., a technetium or rhenium isotope, through the chelating group to form an antibody-radionuclide conjugate which can be employed therapeutically, e.g., in the treatment of malignant tumors, or as an in vivo diagnostic imaging agent.

DETAILED DESCRIPTION AND PREFERRED EMBODIMENTS

Figure 1A:
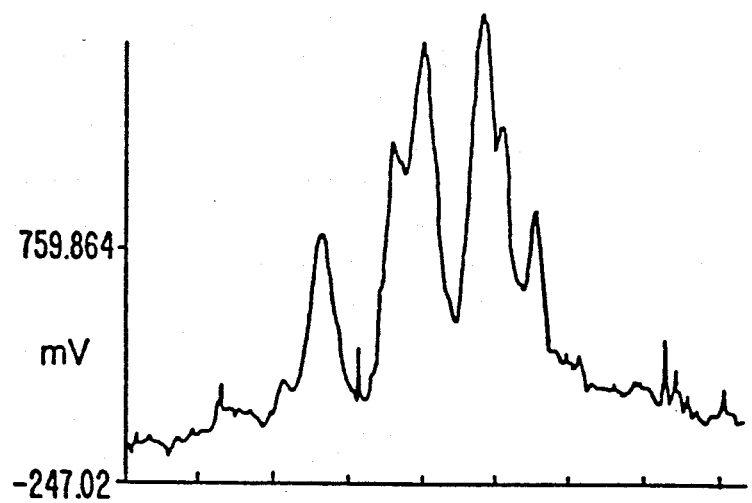
FIG. 1a is a laser densitomer scan from an IEF gel of the conjugate prepared in Example 6 in a pH 5.0 buffer.

The antibody conjugates of formulas I and II are prepared by reacting a bifunctional coupling agent of the invention with an antibody or fragment, that is, a F(ab)'$_2$ or Fab' fragment, of an antibody. The Fab' fragment employed is derived from an antibody which is capable of retaining antigen-binding activity after it has undergone enzymatic and/or chemical treatments which convert the whole antibody to a Fab' fragment. The whole antibody is first treated with an enzyme which effects a site-specific cleavage of the two heavy chains, removing the Fc portion at the carboxyl-terminal ends of the heavy chains. The resultant F(ab)'$_2$ fragment is then treated with a reducing agent, such as dithiothreitol. The reducing agent cleaves disulfide bonds, including the disulfide bonds linking the two heavy chains. Even though the heavy-light chain disulfide bonds may be cleaved, the heavy and light chains remain associated. There are thus produced two Fab' fragments, each having at least one free sulfhydryl group pendent from its heavy chain. The free sulhydryl groups can be alkylated with a blocking agent, such as N-ethyl maleimide, iodoacetamide or iodoacetic acid. By blocking the sulfhydryl groups, they are unavailable to compete for the reaction with the radionuclide. The ε-amino groups of lysine residues serve as reactive sites at which the antibody fragment or whole antibody is joined to the coupling agent to produce the antibody conjugate.

The enzymatic cleavage of antibodies with papain in the presence of a thiol activating agent yields Fab' fragments devoid of inter-heavy chain disulfide bonds that are especially useful in the invention inasmuch as the resulting antibody fragments lack free sulfhydryl groups which otherwise need to be alkylated by a blocking agent.

Antibodies which are useful in the practice of the invention include antibodies to any of the antigens which are known to be effective as in vivo tumor markers such as carcinoembryonic antigen (CEA), alpha-fetoprotein, human chorionic gonadotropin or its beta subunit, colon specific antigen-p, tumor specific glycoprotein and the like.

The antibodies employed can be heterogeneous or they can be monoclonal antibodies. Monoclonal antibodies are produced by selected hybridoma cells produced in accordance with the procedure of G. Kohler and C. Millstein, *Nature (London)*, 256:495–497 [1975]. An example of an antibody for use in producing the Fab' fragments employed in the practice of the invention is a monoclonal antibody to the tumor associated antigen, CEA. This murine monoclonal anti-CEA antibody can be cleaved with preactivated thiol free papain, using the procedure of Parham, et al. (*J. Immunol. Methods*, 53:133–173 [1982]) to produce an F(ab')$_2$ fragment having a single disulfide bond joining the heavy chains. The interchain disulfide bonds are then disrupted by treatment with a reducing agent to produce Fab' fragments. Even in the reduced state, the heavy and light chains remain associated so that the antigen binding activity is retained. The reduction is conveniently carried out by incubation in a buffered solution at or near neutral pH. Temperature of the incubation is not critical and room temperature is suitable. Incubation is generally carried out for about 1 to 2 hours. Dithiothreitol is the preferred reducing agent for the cleavage of the interchain disulfide bonds.

The antibody conjugates of formula I and II are produced by reacting the whole antibody or fragment with a coupling agent of the invention which is represented by the formulas:

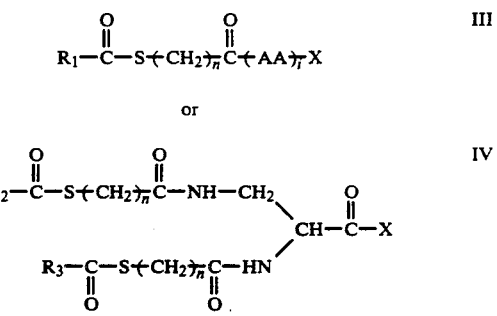

In formulas III and IV, $R_1$, $R_2$, and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently an α or β amino acids linked to each other by amide bonds; i is an integer of from 2 to 6; and X is an activating group capable of forming an amide bond with an ε-amino group of the antibody or fragment thereof. Preferably, X is a member selected from the group consisting of a halogen, $N_3$,

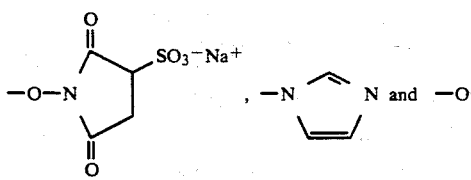, 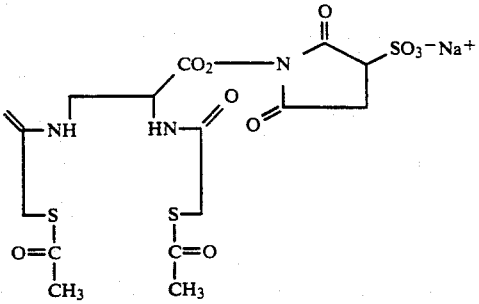

-continued

IVb

The following are exemplary of coupling agents of formula III which can be employed to attach a radionuclide metal ion to the ε-amino group in the antibody:

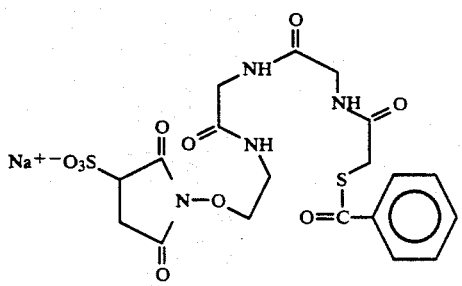

IIIa

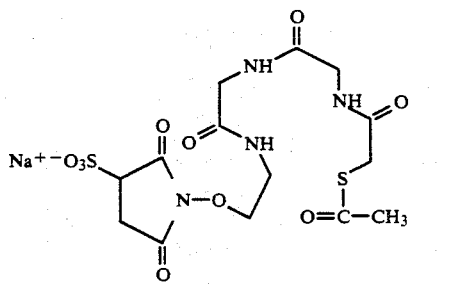

IIIb

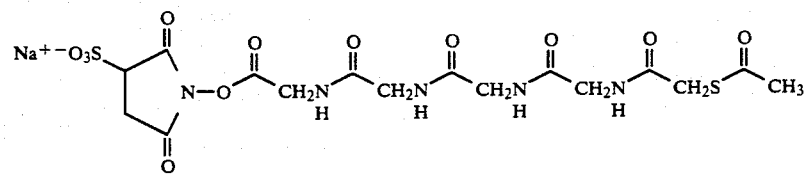

IIIc

The following are exemplary of coupling agents of the formula IV which can be employed to attach the radionuclide metal ion to the ε-amino group of the antibody.

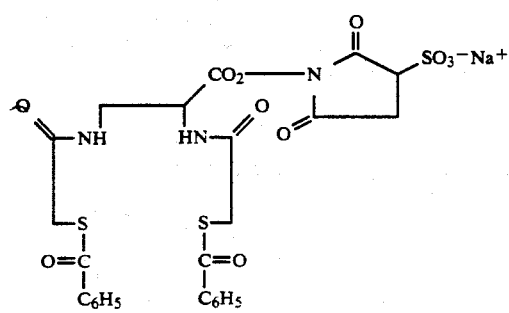

IVa

The coupling agent of formula III of the ester type can be produced by reacting a compound of the formula X—OH with a carboxylic acid of the formula

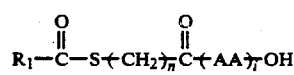

V under conditions which result in esterification of the carboxyl group. The compound of formula V, in turn, can be prepared from the polypeptide H$\pm$(AA$\rightarrow$)$_i$OH. The polypeptide is reacted with a chloroacylchloride, e.g., chloroacetylchloride, to produce a compound of the formula

VI

The compound of formula VI can then be reacted with a compound of the formula

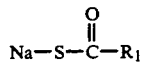

to produce the compound of formula V.

As merely illustrative of the above-described reaction sequence for producing a compound of formula V, one can refer to the following scheme for producing S-benzoylmercaptoacetylglycylglycylglycine:

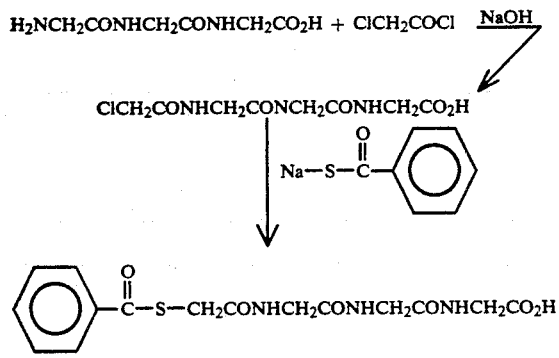

The S-benzoylmercaptoacetylglycylglycylglycinate can then be reacted, for example, with sodium N-hydroxysulfosuccinimide to produce a compound of formula III, i.e., sodium sulfosuccinimidoyl(S-benzoylmercaptoactylglycylglycylglycinate). An analogous reaction scheme, using sodium thioacetate in place of sodium thiobenzoate, produces a sodium sulfosuccinimidoyl (S-acetylmercaptoacetylglycylglycylglycinate).

The couplding agents of formula IV of the ester type can be produced by reacting a compound of the formula X—OH with a carboxylic acid of the formula

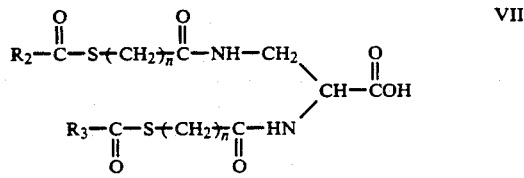

A carboxylic acid of formula VII can be prepared from 2,3-diaminopropanoic acid by procedures analogous to those described by A. R. Fritzerg et al., *J. Nucl. Med.*, 23:592–598 (1982) for the corresponding ethyl ester. The procedure is illustrated in the following reaction scheme:

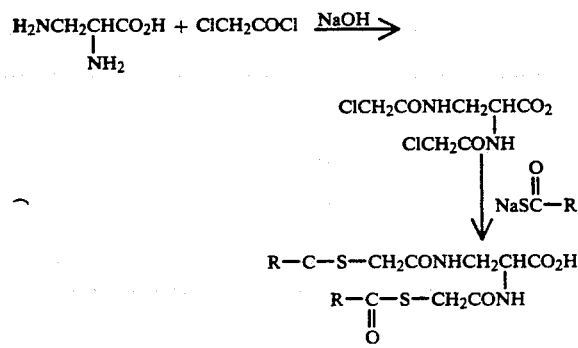

The coupling agent of formula III or IV is reacted with the ε-amino group of the antibody or Fab' fragment to produce, via an amide bond, the antibody conjugate of formula I or II.

The reaction is carried out in neutral or slightly acidic buffers such as 20 mM phosphate, pH 7.0. To avoid undersirable side reactions, amine buffers should be avoided. Temperature of reaction is not critical and is preferably about room temperature. At room temperature, the reaction proceeds to completion in about 1 hour. The product can be isolated by conventional chromatographic means such as by gel filtration chromatography.

The antibody conjugate of formula I or II is complexed with a radionuclide metal ion under chelating conditions to produce an antibody-radionuclide complex. Chelation with Tc-99m or rhenium isotopes can be accomplished by incubating the antibody conjugate with a salt of the desired isotope in a buffered solution. The coupling agent of the invention is especially useful in conjunction with Tc-99m and with isotopes of rhenium, such as rhenium-186, rhenium-188 and rhenium-189.

The antibody radionuclide complex can be formulated in a physiologically acceptable buffer for therapeutic or in vivo diagnostic use. In one embodiment of the invention, the Fab' fragment is of a murine monoclonal antibody to CEA. The CEA-antibody conjugate is chelated with Tc-99m or with a radioisotope of rhenium and employed as an in vivo tumor imaging agent using photoscanning procedures known in the art. The CEA-antibody-radionuclide complex is administered intravenously and the subject is subsequently photoscanned to determine the site of uptake of the radionuclide conjugate in vivo. The methods and compositions of the invention can also be employed to couple radionuclides to protein or polypeptide molecules, other than antibodies, which one wishes to radiolabel for use in in vivo or in vitro diagnostic or therapeutic applications.

The following examples are intended to further illustrate the practice of the invention and are not intended to limit its scope in any way.

EXAMPLE 1

Preparation of S-Benzoylmercaptoacetylglycylglycylglycine

A. Preparation of chloroacetylglycylglycylglycine

To a stirred solution of 2.5 g (0.013 mol) of glycylglycylglycine in 75 ml of 1.0N NaOH in a 500 ml flask under nitrogen at 0° C., a solution of 13.0 g (0.115 mol) of chloroacetyl chloride in 100 ml of ether was added dropwise from one addition funnel while simultaneously 100 ml of 1.0N NaOH was added dropwise from another. After additions were complete, the reaction mixture was stirred for 1.5 hr. at 0° C. The mixture was then acidified with concentrated HCl while cooling. After stirring for an additional 30 min. the mixture was concentrated to one-third volume under reduced pressure at 40° C. The residue precipitated upon cooling in an ice bath. Isolation of the solid gave 2.75 g (78.5%) after two washings.

B. Preparation of S-benzoylmercaptoacetylglycylglycylglycine

The crude chloroacetamido product (1.0 g, 0.037 mol) was dissolved in 300 ml of anhydrous methanol under nitrogen. Sodium thiobenzoate (prepared from 1.10 g (0.0076 mol) of thiobenzoic acid and dry methanol to which 175 mg (0.0076 mol) of sodium had been added) in methanol was added. The reaction mixture was refluxed for 1.5 hr. After removal of solvent under reduced pressure, 2N HCl was added with stirring. The solid was isolated by filtration and washed with CHCl$_3$. Crystallization from methanol gave 1.25 g (90%) of products.

EXAMPLE 2

Preparation of N-(3-Sulfosuccinimidyl) S-Benzoylmercaptoacetylclycylolycylglycinate Sodium Salt To a mixture of 1.18 g (3.20 mmol) of S-benzoylmercaptoacetylglycylglycylglycine and 0.70 g (3.20 mmol) of sodium N-hydroxysulfosuccinimide in 20 ml of N,N-dimethylformamide was added 0.67 g (3.20 mmol) of 1,3-dicyclohexylcarbodiimide. The mixture was mechanically stirred overnight under N$_2$ atmosphere. The mixture was cooled in an ice bath and the solids were removed by filtration through a medium frit. The filtrate was added dropwise to rapidly stirred ethyl acetate (~175 ml) to preciptate the product ester which was collected by filtration, washed with ethyl acetate and transferred while still moist with solvent to a vacuum desiccator and dried under vacuum overnight. The product ester weighed 1.562 g .

To test the activity of the product ester, 0.339 g of the product ester was added to a solution of 0.08 g of benzylamine in 6 ml of water. The mixture was stirred for ½ hour and the precipitate was collected to give 0.25 g of product (93 percent) thus indicating that the ester was at least 93 percent active.

EXAMPLE 3

Preparation of S-Acetylmercaotoacetylclygylclycylglycine

A. Preparation of chloroacetylglycylglycylglycine.

To a stirred solution of 2.5 g (0.013 mol) of glycylglycylglycine in 75 ml of 1.0N NaOH in a 500 ml flask under nitrogen at 0° C., a solution of 13.0 g (0.115 mol) of chloroacetyl chloride in 100 ml of ether was added dropwise from one addition funnel while simultaneously 100 ml of 1.0N NaOH was added dropwise from another After additions were complete, the reaction mixture was stirred for 1.5 hr. at 0° C. The mixture was then acidified with concentrated HCl while cooling. After stirring for an additional 30 min. the mixture was concentrated to one-third volume under reduced pressure at 40° C. The residue precipitated upon cooling in an ice bath. Isolation of the solid gave 2.75 g (78.5%) after two washings.

B. Preparation of S-acetylmercaptoacetylglycylglycylglycine

The crude chloroacetylglycylglycylglycine product (1.0 g, 0.0037 mol) was suspended in 50 ml of anhydrous methanol under nitrogen. Sodium thioacetate (prepared from 0.58 g (0.0076 mol) of thioacetic acid and dry methanol to which 175 mg (0.0076 mol) of sodium had been added) in methanol was added. The reaction mixture was refluxed for 1.5 hr. After removal of solvent under reduced pressure, 2N HCl was added with stirring. The solid was isolated by filtration and washed with CHCl$_3$. Crystallization from methanol/water gave 1.00 g (90%) of product.

EXAMPLE 4

Preparation of N-(3-Sulfosuccinimidyl) S-Acetylmercaptoacetylglycylglycylglycinate Sodium Salt To a mixture of 1.00 g (3.30 mmol) of S-acetylmercaptoacetylglycylglycylglycine and 0.71 g (3.30 mmol) of sodium N-hydroxysulfosuccinimide in 16 ml of N,N-dimethylformamide was added 0.68 g (3.30 mmol) of 1,3-dicyclohexylcarbodiimide. The mixture was mechanically stirred overnight under N$_2$ atmosphere. The mixture was cooled in an ice bath and the solids were removed by filtration through a medium frit. The filtrate was added dropwise to rapidly stirred ethyl acetate (200 ml) to precipitate the product ester which was collected by filtration, washed with ethyl acetate and transferred while still moist with solvent to a vacuum desiccator and dried overnight under high vacuum. The product ester weighed 1.49 g .

The activity of the product ester was tested by adding 0.338 g of the ester to a solution of 0.08 g of benzylamine in 6 ml of water. Stirring was continued for ½ hour and the benzamide was collected by filtration to give 0.238 g product indicating that the ester was at least 90 percent active.

EXAMPLE 5

Preparation of N-(3-Sulfosuccinimidyl) Acetylmercaptoacetylglygylclycylglycylglycinate Sodium Salt A slurry of 1.5 g (4.65 mmol) of N-chloroacetyl-tetraglycine and 0.54 g (4.74 mmol) of potassium thioacetate in 75 ml anhydrous methanol was refluxed for 6.5 hours. The resulting mixture was cooled in an ice bath for ½ hour and then filtered. The white solid was slurried in 10 ml of water for 1 hour at room temperature and refiltered to give 1.11 g (3.07 mmol) of the thioacetyl compound which was characterized by $^{13}$C nmr.

To a mixture of 1.0 g (2.76 mmol) of the thioacetyl compound and 0.60 g (2.76 mmol) of sodium N-hydroxysulfosuccinimide in 25 ml of N,N-dimethylformamide was added 0.57 g (2.76 mmol) of 1,3-dicyclohexylcarbodiimide. The resulting slurry was stirred at room temperature for 15 hours. Ten milliliters of acetone was added and the reaction mixture was cooled in an ice bath for ½ hour. The solid was filtered and discarded. To the filtrate was added 150 ml of dry ether and the solid was filtered. The product ester material was dried under vacuum to give 0.39 g (0.71 mmol) of a light tan solid which was characterized by $^{13}$C nmr.

Further derivatization was carried out by reacting 100mg (0.18 mmol) of the product ester with 0.02 ml (0.18 mmol) of benzylamine in 1ml of N,N-dimethylformamide for 4 hours at 25° C. The reaction mixture was diluted with 20 ml anhydrous ether and filtered. After drying under vacuum, 77 mg (0.17 mmol) of a white solid was obtained and confirmed by $^{13}$C nmr to be the desired product ester.

EXAMPLE 6

Preparation of Conjugate of Ribonuclease A (RN) Type XII-A and N-(3-Sulfosuccinimidyl) S-Benzoylmercaptoacetylglycylglycylglycinate The Ribonuclease A (RN) Type XII-A (hereinafter referred to as RN) that was used is commercially available from Sigma Corp. of St. Louis, Mo. Two hundred fifty μl of 10 mg/ml RN dissolved in a pH 5 buffer (made from 100 mM citrate/100 mM phosphate) was incubated at room temperature for ½ hour with 250μl of 30 mM of N-(3-sulfosuccinimidoyl) S-benzoylmercaptoacetylglycylglycylglycinate sodium salt also dissolved in the pH 5.0 buffer. After the incubation period, the sample was analyzed by pH 3-10 agarose isoelectric focussing (AGIEF).

FIG. 1a presents laser densitomer scans of the conjugate analyzed by AGIEF.

Figure 1B:
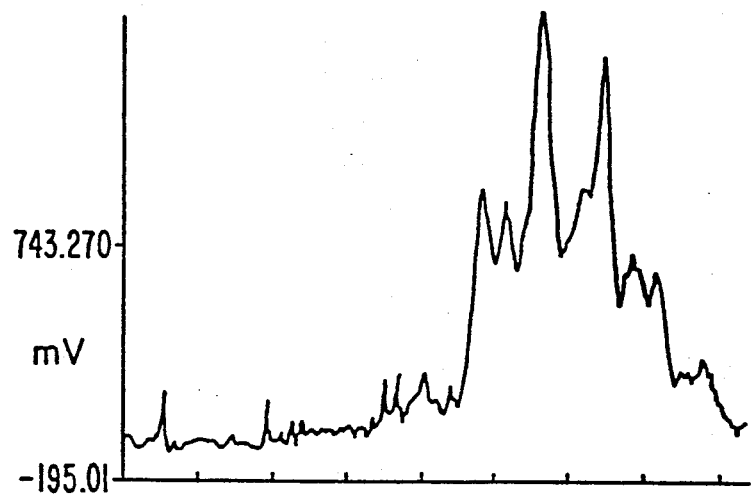
FIG. 1b is a laser densitomer scan from an IEF gel of the conjugate prepared in Example 6 in a pH 6.0 buffer.

The above preparation was repeated with the exception that the buffer used had a pH of 6. FIG. 1b presents laser densitomer scans of the conjugate (prepared with 6.0 pH buffer) analyzed by AGIEF.

Figure 1C:
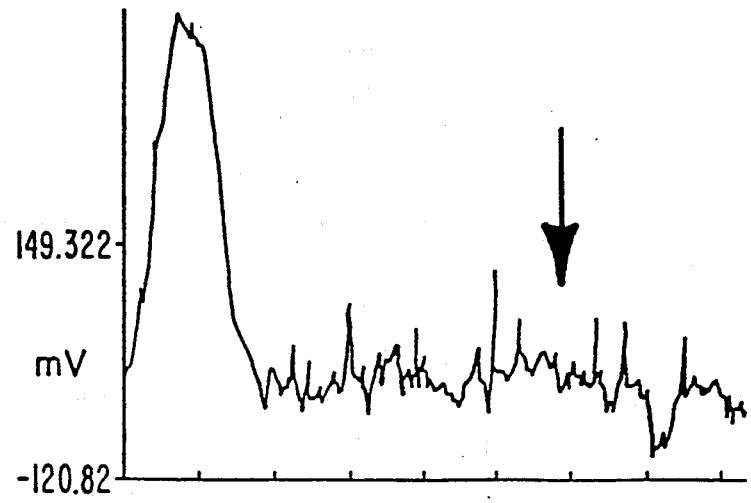
FIG. 1c is a laser densitomer scan from an IEF gel of unreacted ribonuclease A(RN) Type XII-A in a pH 5.0 buffer.

As a control, unreacted RN in a pH 5.0 buffer was analyzed by AGIEF. FIG. 1c presents laser densitomer scans of the unreacted RN sample analyzed by AGIEF.

FIG. 1a demonstrates that the protein reacted at pH 5.0 shows a significantly different focussing pattern than the unreacted control (FIG. 1c). This is attributed to the successful reaction of the chelate with the RN lysine groups. The net result is a decrease in the overall positive charge of the protein indicated by the observed anodal migration of the chelate reacted sample. The pH 6.0 reacted sample (FIG. 1b) also shows this same trend but to an even greater extent.

EXAMPLE 7

Preparation of Conjugate of Antibody Dimer and N-(3-Sulfosuccinimidyl) S-Acetylmercaptoacetylglycylglycylglycinate Sodium Salt A monoclonal antibody to a breast tumor antigen, MAB 72.3, was digested with papain to yield the F(ab)'$_2$ dimer. A series of B72.3 dimer-chelate conjugates were prepared at chelate/protein molar ratios of 20/1 and 100/1 at pHs of 5.0 and 8.0. The conjugates were prepared as follows: 20 μl of 4.46 mg/ml of B72.3 dimer in pH 5.0 or 8.0 (made from 100 mM citrate/100 mM phosphate) was mixed with 5 μl of 3.57 mM or 17.85 mM of N-(3-sulfosuccinimidyl S-acetylmercaptoacetylglycylglycylglycinate sodium salt dissolved in the desired pH buffer. Incubation proceeded for 1½ hour at room temperature after which time the samples were analyzed by pH 3-10 AGIEF (as per Example 6).

Figure 2A:
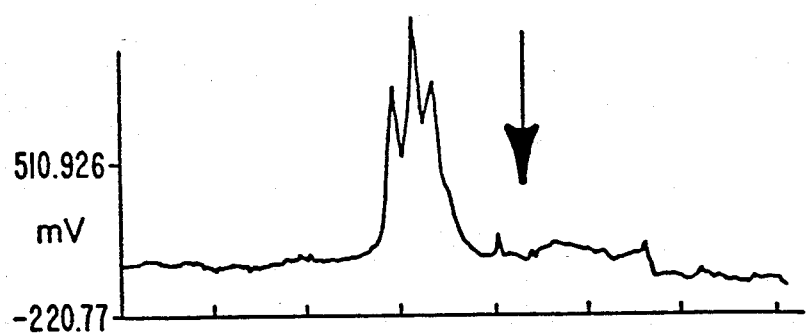
FIG. 2a is a laser densitomer scan from an IEF gel of unreacted monoclonal antibody B72.3 dimer in pH 5.0 buffer.

As a control, unreacted B72.3 dimer in pH 5.0 buffer was analyzed by pH 3-10 AGIEF. FIG. 2a presents laser densitomer scans of unreacted B72.3 dimer in pH 5.0 buffer.

Figure 2B:
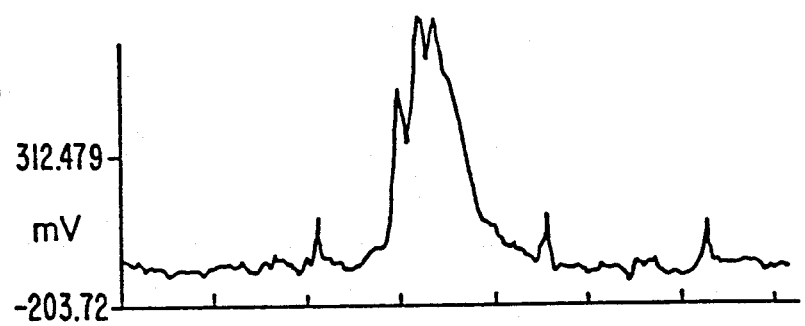
FIG. 2b is a laser densitomer scan from an IEF gel of the conjugate prepared in Example 5 in a pH 5.0 buffer and at a molar ratio of chelate/B72.3 dimer of 20/1.

FIG. 2b presents the laser densitomer scans of the B72.3 dimer-chelate conjugate at pH 5.0 at a molar ratio of chelate/B72.3 equaling 20/1.

Figure 2C:
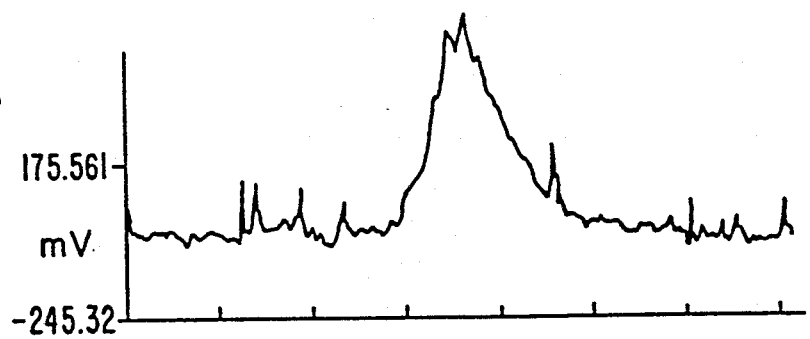
FIG. 2c is a laser densitomer scan from an IEF gel of the conjugate prepared in Example 5 at pH 8.0 and at a molar ratio of chelate/B72.3 dimer of 20/1.

FIG. 2c presents the laser densitomer scans of the B72.3 dimer-chelate conjugate at pH 8.0 at a molar ratio of chelate/B72.3 dimer equaling 20/1.

Figure 2D:
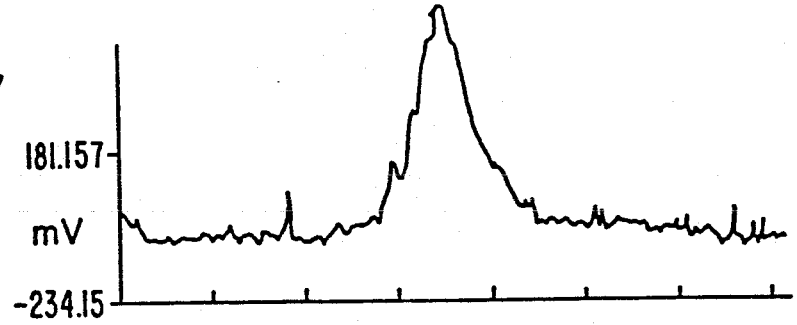
FIG. 2d is a laser densitomer scan from an IEF gel of the conjugate prepared in Example 5 at pH 5.0 and at a molar ratio of chelate/B72.3 dimer of 100/1.

FIG. 2d presents the laser densitomer scans of the B72.3 dimer-chelate conjugate at pH 5.0 at a molar ratio of chelate/B72.3 dimer equaling 100/1.

Figure 2E:
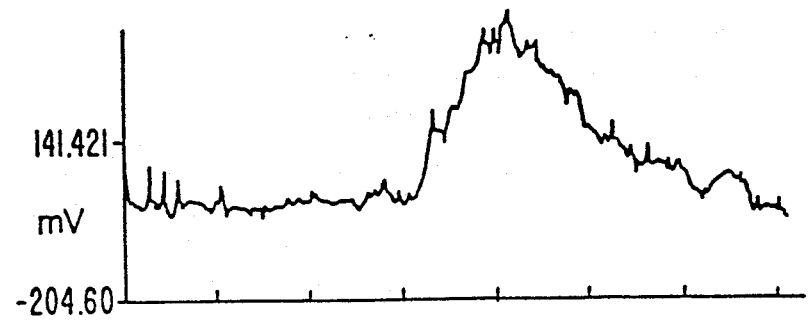
FIG. 2e is a laser densitomer scan from an IEF gel of the conjugate prepared in Example 5 at pH 8.0 and at a molar ratio of chelate/B72.3 dimer of 100/1.

FIG. 2e presents the laser densitomer scans of the B72.3 dimer-chelate conjugate at pH 8.0 at a molar ratio of chelate/B72.3 dimer equaling 100/1.

EXAMPLE 8

Preparation of Conjugate of Anti-CEA Fab' and N-(3-Sulfosuccinimidyl) S-Benzoylmercaptoacetylglycylglycylglycinate Sodium Salt A monoclonal antibody to carcinoembryonic antigen (CEA) was treated with papain to remove the $F_c$ portion and subsequently reduced with dithiothreitol to produce Fab' monomer fragments. The free sulfhydryl groups of the Fab' fragments were blocked by treatment with tritiated N-ethylmaleimide. Twenty μl of anti-CEA Fab' monomer at 4.55 mg/ml in pH 5.0 or 8.0 buffer (made from 100 mM citrate/100 mM phosphate) was incubated for 1½ hours with 5 μl of 17.85 mM of N-(3-sulfosuccinimidyl S-benzoylmercaptoacetylglycylglycylglycinate sodium salt which was dissolved in the appropriate pH buffer giving a chelate/protein molar ratio of 100/1. After the incubation period, samples were analyzed by size-exclusion HPLC (SEC-HPLC). Results of the HPLC were consistent with the formation of the antibody-coupling agent conjugate.

In order to determine whether the conjugate retained antigen binding activity, a suspension radioimmunoassay was carried out using I-125 labeled CEA as the antigen. The binding profile that was obtained was virtually superimposable on a profile that was obtained using unconjugated Fab' anti-CEA as the antibody. Thus, the conjugated Fab' fragment retained its antigen-binding capacity.

EXAMPLE 9

Preparation of Conjugate of Anti-CEA Fab' and N-(3-Sulfosuccinimidyl) S-Acetylmercaptoacetylglycylglycylglycinate Sodium Salt Anti-CEA Fab' fragments containing blocked sulfhydryl groups, were prepared as described in Example 6. Twenty μl of anti-CEA Fab' at 4.55 mg/ml in pH 5.0 or 8.0 buffer (made from 100 mM citrate/100 mM phosphate) was incubated for 1½, hour with 5 μl of 17.85 mM of N-(3sulfosuccinimidyl) S-acetylmercaptoacetylglycylglycylglycinate sodium salt dissolved in the appropriate pH buffer giving a chelate/protein molar ratio of 100./1 After the incubation period, samples were analyzed by SEC-HPLC. Results of the HPLC were consistent with the formation of the antibody-coupling agent conjugate.

EXAMPLE 10

Preparation of Antibody-Tc-99m Complex

Anti-CEA Fab', containing blocked sulfhydryl groups as described in Example 6, at a final concentration of ~3 mg/ml in 25 mM PO$_4$ buffer pH 7.4, is reacted with varying amounts of N-(3-sulfosuccinimidyl) S-benzoylmercaptoacetylglycylglycylglycinate sodium salt in 100 mM NaPO$_4$ pH 8.0 to yield molar ratios of 250/1 to 10/1 (chelate/protein). Incubation proceeds for 2 hours at room temperature. After antibody incubation with the chelate, excess acylation reagent is removed by spin-column centrifugation. Electrolytic reduction reaction vials containing 50 mg each of 4,5-dihydroxy-1,3-benzenedisulfonic acid (tiron), 1 ml water adjusted to pH 7.0 with saturated sodium bicarbonate, and 1 ml of sodium 99m-pertechnetate from a technetium generator are sealed and purged with argon for 5 min. Two zirconium electrodes are inserted into the vial, the vial inverted and a current of 100 mM and 10 volts is passed through the solution for 2 min. The resulting Tc-99m-tiron complex is incubated with the chelate-antibody conjugate to produce Tc-99m-chelate-antibody complex.

EXAMPLE 11

Biodistribution of Antibody-Tc-99m Complex and I-125Nonspecific Fab' Fragments

In vivo studies were performed in 12-16 week-old Sprague-Dawley rats, which were obtained from Harlin Sprague Dawley, Inc. (Indianapolis, Ind.). Each animal received a co-injection pair of monoclonal antibodies, i.e., an anti-CEA Fab'-Tc-99m complex of the present invention and an anti-CEA Fab' fragment which had been labeled with I-125 by the chloramine T method. The latter member of the injectate was included for all studies in an effort to normalize each experiment. The animals were sacrified at 2-4 or 18-24 hours post-injection. Dual label radionuclide analysis of blood, urine, liver and kidney(s) was performed in a gamma counter.

The first antibody complex that was tested was a complex of anti-CEA Fab'/N-(3-sulfosuccinimidyl) S-benzoylmercaptoacetylglycylglycylglycinate sodium salt/99mTc. In the following table, this complex is identified as #10/MAb/Tc.

The second antibody complex that was tested was a complex of anti-CEA Fab'/N-(3-sulfosuccinimidyl) 2,3-bis(acetylmercaptoacetamido)propionate sodium salt/99mTc. In the following table, this complex is identified #9/MAb/Tc.

Table I below summarizes the percentage of injected dose of radioactivity remaining in the blood, urine, liver and kidney as a function of time.

TABLE 1

| Injectate | m/Blood 2-4 h | m/Blood 18-24 h | Urine 2-4 h | Urine 18-24 h | Liver 2-4 h | Liver 18-24 h | Kidney (One) 2-4 h | Kidney (One) 18-24 h |
|---|---|---|---|---|---|---|---|---|
| #10/MAb/Tc | 2.30 | 1.12 | 5.12 | 51.04 | 0.66 | 0.71 | 1.89 | 4.01 |
| I-125/MAb | 2.40 | 1.12 | 3.75 | 76.00 | 0.54 | 0.59 | 1.01 | 0.22 |
| #9/MAb/Tc | 1.84 | 1.31 | 8.99 | 43.63 | 0.87 | 4.73 | 2.06 | 5.38 |
| I-125/MAb | 2.34 | 0.97 | 3.57 | 70.68 | 0.61 | 0.59 | 1.18 | 0.20 |

EXAMPLE 12

Preparation of N-(3-Sulfosuccinimidyl) 2,3-Bis (Acetylmercaptoacetamido)propionate A mixture of 2,3-bis(acetylmercaptoacetamido) propionic acid (431.7 mg), N-hydroxysulfosuccinimide (293 mg) and 1,3-dicyclohexylcarbodiimide (278 mg) in 5 ml of anhydrous dimethylformamide was stirred for 18 hours at room temperature. The reaction mixture was diluted with acetone (15 ml) and filtered. The filtrate was then poured onto ether (200 ml) and the precipitate was filtered and dried (vacuum desiccator). The product which was extremely hygroscopic, was kept in a desiccator at all times. Yield, 360 mg.

EXAMPLE 13

Preparation of Conjuqate of Anti-CEA Fab' and N-(3-Sulfosuccinimidyl) 2,3-Bis(Acetylmercaptoacetamido)propionate The dimer fragment, F(ab')$_2$, of a monoclonal antibody to CEA was reacted with dithiothreitol and subsequently alkylated with tritiated N-ethylmaleimide to produce the monomer species, Fab'. The anti-CEA Fab' was then conjugated to N-(3-sulfosuccinimidyl-) 2,3-bis-(acetylmercaptoacetamido)propionate using a conjugation reaction similar to that described in Example 6. The conjugate, along with an unreacted control, was analyzed by AGIEF and the resulting gel stained for protein. The dried gel was stained for radioactivity using a Bioscan 200 Imaging System to generate plots. The observed progressive anodal migration of the sample relative to the unreacted control was consistent with the formation of the conjugate.

EXAMPLE 14

Biodistribution of Antibody-Tc-99m Complex and I-125Nonspecific Fab' Fragments

The antibody-coupling agent conjugate produced in Example 13 was reacted with Tc-99m in a manner similar to that described in Example 8. Using procedures similar to those described in Example 9, biodistribution studies were performed in Sprague-Dawley rats to compare the 2-hr. and 22-hr. distribution of the antibody-Tc-99m complex with that of anti-CEA Fab' which had been I-125 labeled using the chloramine T method.

| | 2 HOURS | | 22 HOURS | |
|---|---|---|---|---|
| | Mab/Tc | I-125 | Mab/Tc | I-125 |
| R. Kidney | 1.96 | 1.13 | 5.42 | 0.23 |
| L. Kidney | 2.16 | 1.22 | 5.34 | 0.16 |
| Liver | 0.87 | 0.61 | 4.73 | 0.59 |
| Blood | 1.89 | 2.35 | 1.31 | 0.97 |
| Urine | 8.92 | 3.52 | 43.15 | 69.78 |

Although the foregoing invention has been described in some detail by way of illustration and example for purposes of clarity and understanding, it will be obvious that certain changes and modifications may be practiced within the scope of the appended claims.

What is claimed is:

1. A coupling agent for joining a radionuclide metal ion with a biologically useful protein or polypeptide molecule comprising a compound of the formulas:

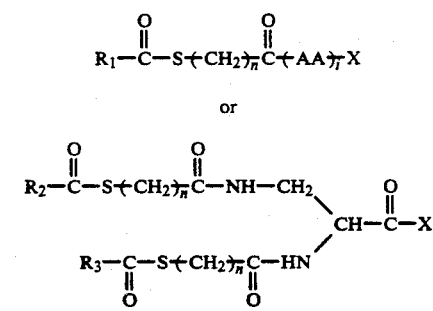

wherein $R_1$, $R_2$, and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently α or β amino acids linked to each other by amide bonds; i is an integer of from 2 to 6; and X is a activating group capable of forming an amide bond with an ε-amino group of said biologically useful protein or polypeptide molecule.

2. The coupling agent of claim 1 wherein X is a member selected from the group consisting of a halogen, $N_3$,

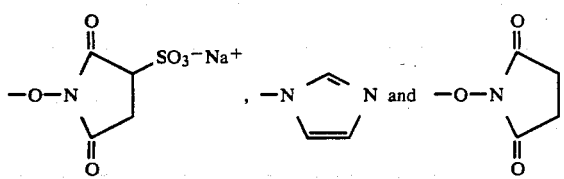

3. The coupling agent of claim 2 wherein X is

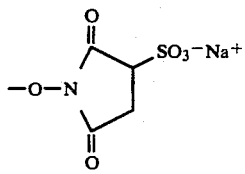

4. The coupling agent of claim 3 wherein i is 3 or 4.
5. The coupling agent of claim 4 wherein $R_1$ is methyl or phenyl.
6. An antibody conjugate of the formula:

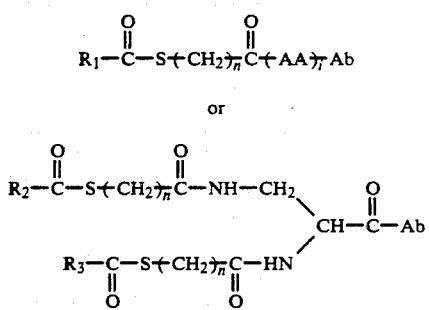

wherein Ab is the residue of an antibody or fragment thereof; and $R_1$, $R_2$, and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently $\alpha$ or $\beta$ amino acids linked to each other by amide bonds; and i is an integer of from 2 to 6.

7. The antibody conjugate of claim 6, wherein Ab is the residue of a F(ab')$_2$ fragment of a monoclonal antibody.

8. The antibody conjugate of claim 6, wherein Ab is the residue of a Fab' fragment of a monoclonal antibody to a tumor associated antigen.

9. The antibody conjugate of claim 6, wherein Ab is the residue of a Fab' fragment of a monoclona antibody to CEA.

10. The antibody conjugate of claim 6, wherein i is 3 or 4.

11. The antibody conjugate of claim 6, wherein $R_1$ is methyl or phenyl.

12. The compound N-(3-sulfosuccinimidyl) S-acetylmercaptoacetylglycylglycylglycinate sodium salt.

13. The compound N-(3-sulfosuccinimidyl) S-benzoylmercaptoacetylglycylglycylglycinate sodium salt.

14. An antibody-radiounuclide complex comprising the antibody conjugate of claim 6 and a radionuclide metal selected from radioisotopes of technetium and rhenium.

15. An antibody-radionuclide complex as claimed in claim 19, wherein the radionuclide is selected from Tc-99m, Re-186, Re-188 and Re-189.

16. The antibody complex of claim 14, wherein Ab is the residue of a F(ab')$_2$ fragment of a monoclonal antibody.

17. The antibody complex of cliam 14, wherein Ab is the residue of a Fab' fragment of a monoclonal antibody to a tumor associated antigen.

18. The antibody complex of claim 14, wherein Ab is the residue of a Fab' fragment of a monoconal antibody to CEA.

19. The antibody complex of claim 14, wherein i is 3 or 4.

20. The antibody complex of claim 19, wherein $R_1$ is methyl or phenyl.

21. A method of detecting and localizing a tumor in vivo which comprises parenterally administering to a subject an antibody-radionuclide complex of claim 19 and photoscanning the subject to determine the site of the antibody complex in vivo.

22. The method of claim 21, wherein the antibodyradionuclide complex is administered intravenously.

23. A method of producing an antibody conjugate for in vivo diagnostic or therapeutic use which comprises:
(a) enzymatically cleaving the Fc fragment from an antibody to a tumor-associated antigen which cleaves to produce an F(ab)'$_2$ dimer;
(b) reducing the F(ab)'$_2$ dimer to produce two Fab' fragments; and
(c) reacting the Fab' fragments with a coupling agent of the formula:

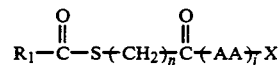

or

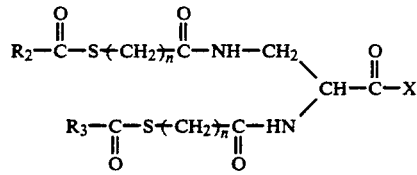

wherein $R_1$, $R_2$ and $R_3$ are the same or different and each represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, or alkoxy, carboxy or sulfonate groups; n is either 1 or 2; AA are independently $\alpha$ or $\beta$ amino acids linked to each other by amide bonds; i is an integer of from 2 to 6; and X is an activating group capable of forming an amide bond with an $\epsilon$-amino group of said Fab' fragment.

24. The method of claim 23, wherein X is a member selected from the group consisting of a halogen, N$_3$,

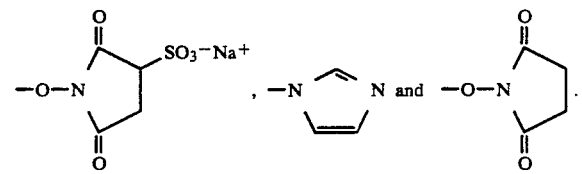

25. The method of claim 23, wherein the antibody is cleaved with preactivated papain.

26. The method of claim 23, wherein the antibody is a monoclonal antibody to CEA.

27. The method of claim 23 wherein i is 3 or 4.

28. The method of claim 23, wherein $R_1$ is methyl or phenyl.

29. A coupling agent for joining a radionuclide metal ion with a biologically useful protein or polypeptide molecule comprising a compound of the formula:

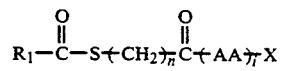

wherein $R_1$ represents a radical selected from the group consisting of alkyls having from 1 to 6 carbon atoms, aryls having from 6 to 8 carbon atoms and alkaryls having 7 to 9 carbon atoms, any of which can be substituted with one or more hydroxyl, alkoxy, carboxy or sulfonate groups; n is either 1 or 2; AA are independently $\alpha$ or $\beta$ amino acids linked to each other by amide bonds; i is an integer of from 2 to 6; and X is a activating group capable of forming an amide bond with an $\epsilon$-amino group of said biologically useful protein or polypeptide molecule.

* * * * *